United States Patent
Madin et al.

(10) Patent No.: US 8,226,604 B2
(45) Date of Patent: Jul. 24, 2012

(54) NEEDLESTICK PREVENTION DEVICE

(75) Inventors: Graham John Madin, Mielkendorf (DE); Marc Andrew Koska, Sussex (GB)

(73) Assignee: Star Syringe Limited, London (GB)

( * ) Notice: Subject to any disclaimer, the term of this patent is extended or adjusted under 35 U.S.C. 154(b) by 99 days.

(21) Appl. No.: 12/171,795

(22) Filed: Jul. 11, 2008

(65) Prior Publication Data
US 2009/0018510 A1 Jan. 15, 2009

Related U.S. Application Data

(60) Provisional application No. 60/970,134, filed on Sep. 5, 2007.

(30) Foreign Application Priority Data

Jul. 12, 2007 (GB) .................................. 0713580.9
Jun. 12, 2008 (GB) .................................. 0810753.4

(51) Int. Cl.
*A61M 5/00* (2006.01)
(52) U.S. Cl. ........................................ 604/110; 604/192
(58) Field of Classification Search .................. 604/192, 604/110, 198
See application file for complete search history.

(56) References Cited

U.S. PATENT DOCUMENTS

| | | | |
|---|---|---|---|
| 4,944,397 A | 7/1990 | Miller | |
| 5,733,265 A * | 3/1998 | Bachman et al. | 604/263 |
| 5,885,249 A | 3/1999 | Irisawa | |
| 5,919,165 A | 7/1999 | Benson | |
| 6,120,482 A | 9/2000 | Szabo | |
| 6,298,541 B1 | 10/2001 | Newby et al. | |
| 6,436,086 B1 | 8/2002 | Newby et al. | |
| 6,440,104 B1 | 8/2002 | Newby et al. | |
| 6,582,397 B2 | 6/2003 | Alesi et al. | |
| 6,648,855 B2 | 11/2003 | Crawford et al. | |
| 6,695,819 B2 | 2/2004 | Kobayashi | |
| 6,699,217 B2 | 3/2004 | Bennett et al. | |
| 6,752,788 B2 | 6/2004 | Tuen | |
| 6,780,169 B2 | 8/2004 | Crawford | |
| 6,837,877 B2 | 1/2005 | Zurcher | |
| 6,869,418 B2 | 3/2005 | Marano-Ford | |
| 6,921,388 B2 | 7/2005 | Swenson | |
| 7,128,726 B2 | 10/2006 | Crawford et al. | |
| 7,201,736 B2 | 4/2007 | Hauri | |
| 7,223,258 B2 | 5/2007 | Crawford | |

(Continued)

FOREIGN PATENT DOCUMENTS
EP 0649382 4/1995
(Continued)

*Primary Examiner* — Kevin C Sirmons
*Assistant Examiner* — Brandy C Scott
(74) *Attorney, Agent, or Firm* — Michael Best & Friedrich LLP

(57) ABSTRACT

A needlestick prevention device for an injection device having a hollow needle comprises a sheath for attachment to the injection device. The sheath has three positions. In a first, inoperative position the sheath sealingly encloses the needle. In a second operative position a first part of the sheath is removed, a second part remains attached to the injection device and a third part is pivoted about a hinge to expose the needle. In a third, cover position the third part is pivoted about the hinge to cover at least the tip of the needle and is retained in position by a retaining device acting between the second part and the third part. The needlestick prevention device is simple to manufacture and use.

11 Claims, 7 Drawing Sheets

U.S. PATENT DOCUMENTS

| | | |
|---|---|---|
| 7,250,038 B2 | 7/2007 | Simpson et al. |
| 2002/0072715 A1 | 6/2002 | Newby et al. |
| 2002/0091360 A1* | 7/2002 | Peters, III .................. 604/198 |
| 2002/0099342 A1 | 7/2002 | Zurcher |
| 2002/0151852 A1 | 10/2002 | Crawford et al. |
| 2002/0151853 A1 | 10/2002 | Crawford |
| 2002/0161336 A1 | 10/2002 | Crawford et al. |
| 2003/0125676 A1 | 7/2003 | Swenson et al. |
| 2003/0181873 A1 | 9/2003 | Swenson |
| 2003/0187399 A1 | 10/2003 | Crawford |
| 2003/0220614 A1 | 11/2003 | Crawford |
| 2003/0229320 A2 | 12/2003 | Zurcher |
| 2004/0054334 A1 | 3/2004 | Prais et al. |
| 2004/0059302 A1 | 3/2004 | Crawford et al. |
| 2004/0186438 A1* | 9/2004 | Hudon ..................... 604/192 |
| 2004/0186439 A1 | 9/2004 | Crawford et al. |
| 2004/0211689 A1 | 10/2004 | Torris et al. |
| 2005/0124944 A1 | 6/2005 | Hwang |
| 2005/0148942 A1 | 7/2005 | Newby et al. |
| 2005/0245879 A9 | 11/2005 | Crawford |
| 2006/0052748 A1 | 3/2006 | Coelho et al. |
| 2006/0149188 A1 | 7/2006 | Simas, Jr. |
| 2006/0200078 A1 | 9/2006 | Konrad |
| 2006/0224122 A1 | 10/2006 | Bosel et al. |
| 2006/0270979 A1 | 11/2006 | Simas, Jr. et al. |
| 2007/0016146 A1 | 1/2007 | Yang |
| 2007/0156088 A1 | 7/2007 | Hauri |

FOREIGN PATENT DOCUMENTS

| | | |
|---|---|---|
| EP | 0702973 | 3/1996 |
| EP | 0744183 | 11/1996 |
| EP | 0819441 | 1/1998 |
| EP | 0862920 | 9/1998 |
| EP | 0885621 | 12/1998 |
| EP | 0887082 | 12/1998 |
| GB | 2259254 | 3/1993 |
| WO | 87/07162 | 12/1987 |
| WO | 93/16745 | 9/1993 |
| WO | 01/78813 | 10/2001 |
| WO | 2005/030290 | 4/2005 |
| WO | 2006/041442 | 4/2006 |
| WO | 2007/047328 | 4/2007 |

\* cited by examiner

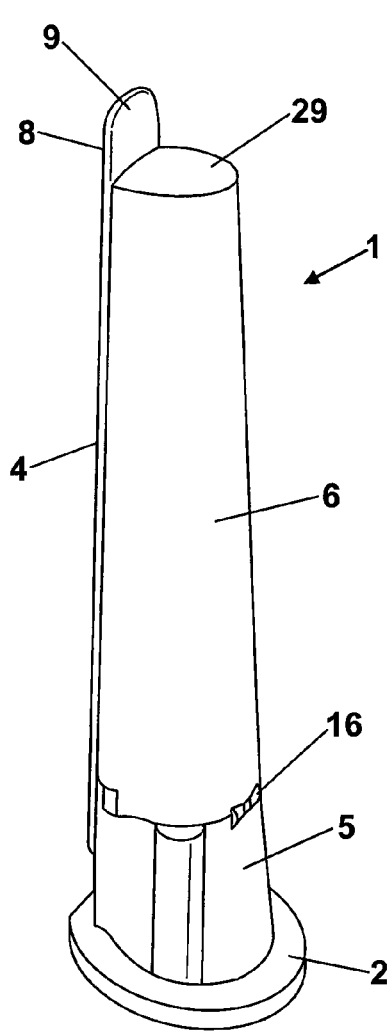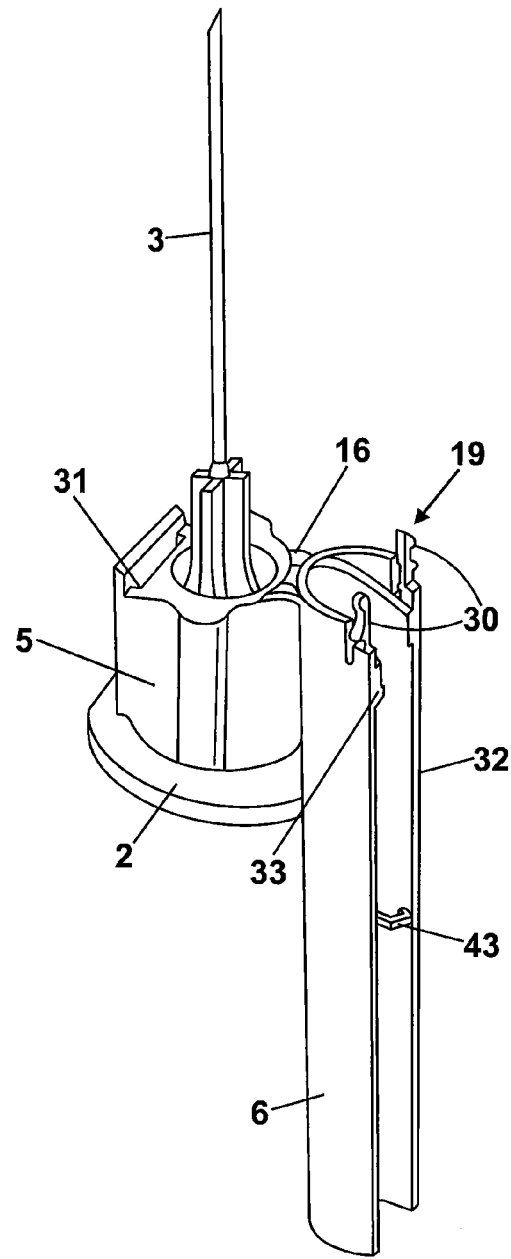
*Fig. 8*
*Fig. 9*

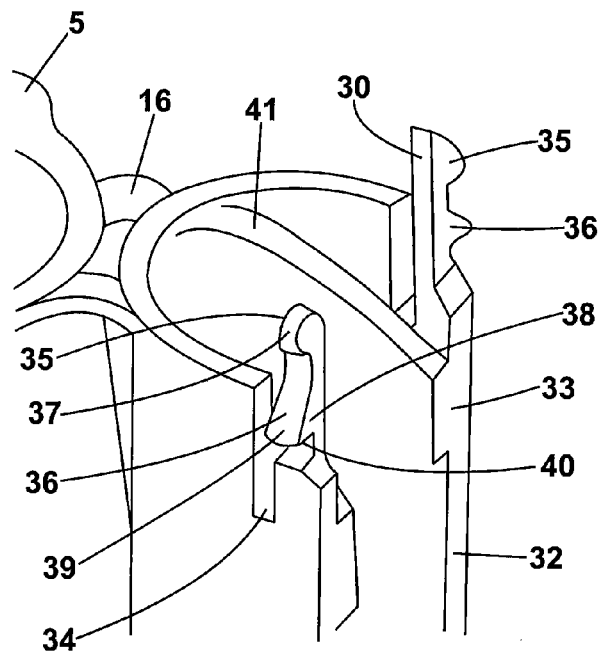
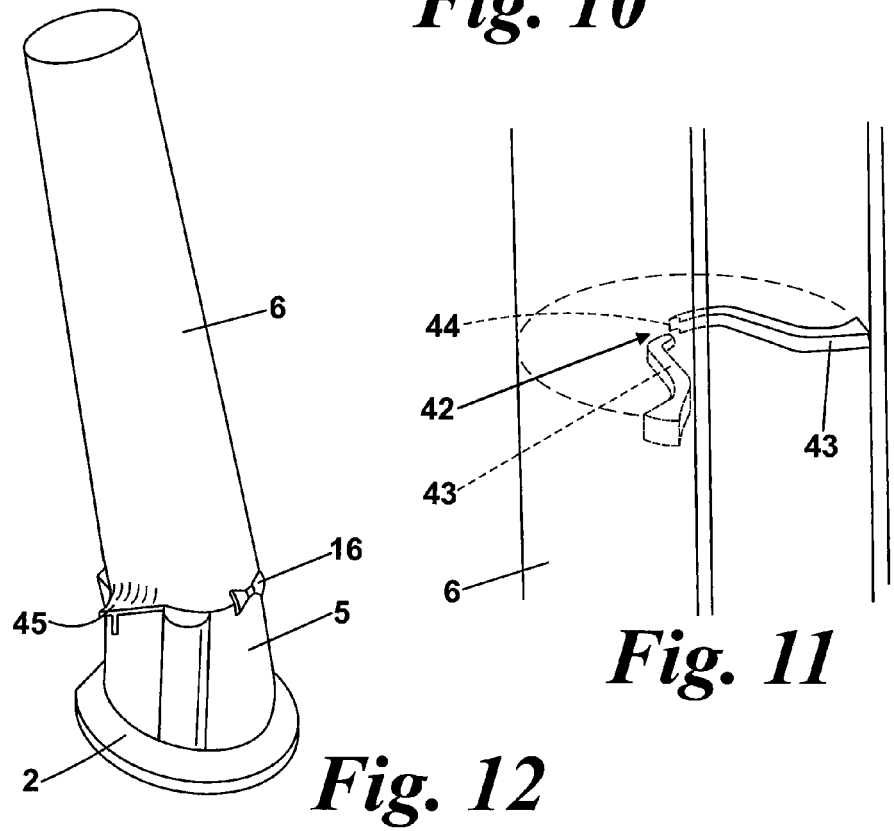
Fig. 10
Fig. 11
Fig. 12

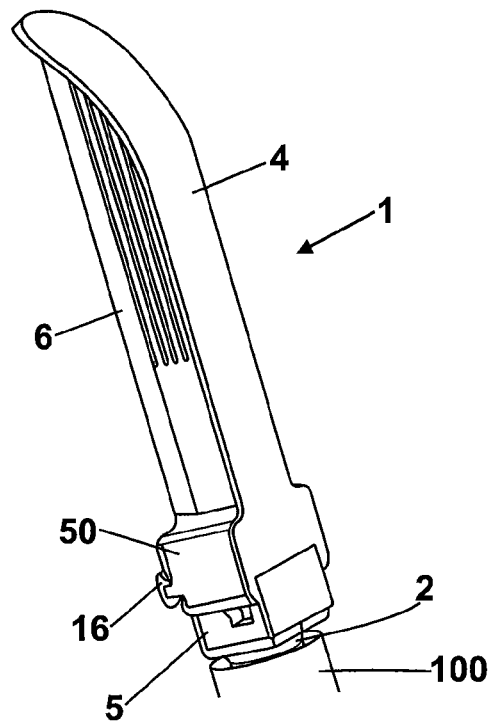
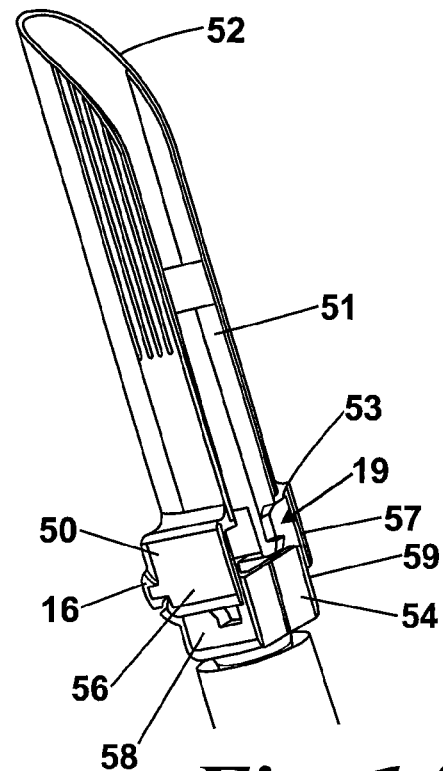
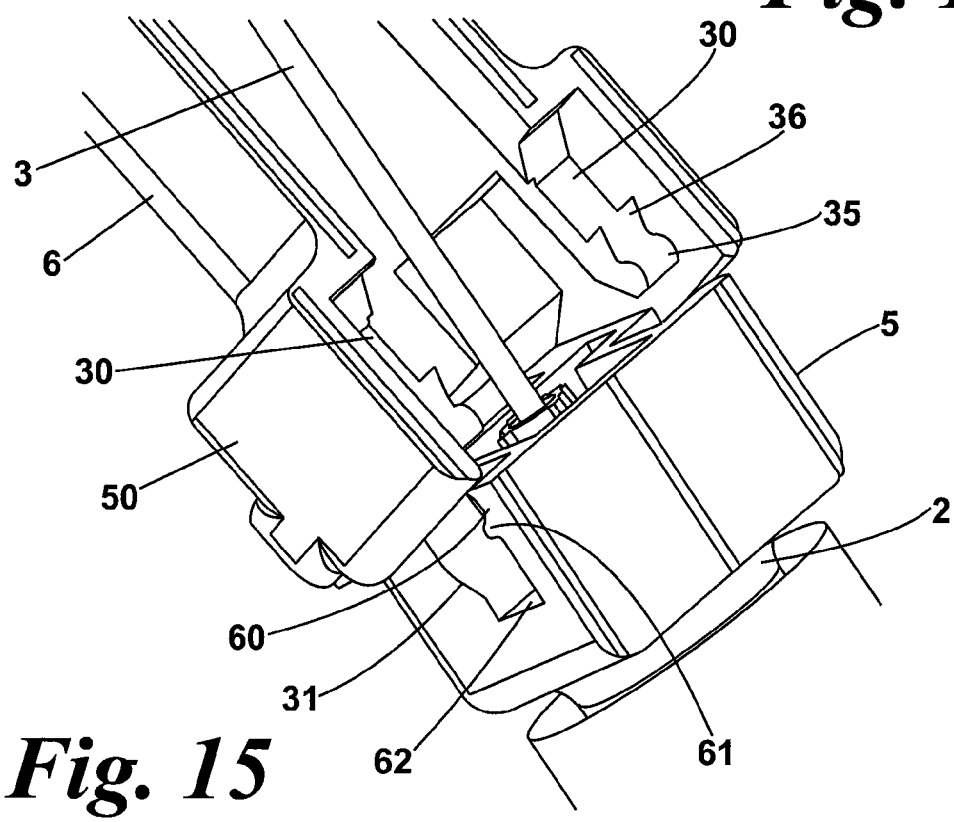

NEEDLESTICK PREVENTION DEVICE

CROSS-REFERENCE TO RELATED APPLICATIONS

This application claims the benefit of U.S. Provisional Patent Application No. 60/970,134, filed Sep. 5, 2007, now pending, and claims priority to Great Britain Patent No. 0713580.9, filed Jul. 12, 2007 and Great Britain Patent No. 0810753.4, filed Jun. 12, 2008. The entire contents of each of the foregoing applications are incorporated herein by reference.

BACKGROUND

This invention relates to a needlestick prevention device for use with injection devices, such as syringes.

A needlestick injury generally occurs in a medical environment, and particularly before or after use of a syringe or other injection device, when the user accidentally sticks the needle into himself or herself, or indeed another person. It is of course important to prevent such injuries, since they can spread infections and diseases, as well as being painful and possibly incapacitating.

There are several known ways of trying to prevent needlestick injuries. For example, some syringes are made with needles which are retracted automatically after use by means of a spring in the syringe. However, this requires a complex construction, and is expensive to manufacture. Further, it does not address the possibility of injury occurring before the injection is given.

Another known way is to replace the tubular sheath which is supplied with the syringe, protecting the needle. It is not now recommended practice to replace the sheath after the syringe has been used, because of the difficulty of placing the end of the needle accurately in the sheath. It is thought that trying to re-sheath the needle has actually been the cause of a significant number of needlestick injuries. Further, the sheath can easily be removed again, so that injury is possible.

Yet another known needlestick prevention device is an automatic needle sheath mounted on the syringe barrel, the sheath being able to slide out to cover the needle. EP-A-0 268 445 shows a construction with a stationary sheath part, and a movable sheath part spring-biassed to an extended position in which it covers the needle. The movable sheath part retracts to expose the needle for use, and when the retracting pressure is released the spring moves it automatically into its extended position, where it is locked. The movable sheath part has a projection received in a track in the stationary part to determine its movement and to lock it. Again, this is a relatively complex construction which is expensive to manufacture. A similar construction is found in WO 03/105935.

SUMMARY OF THE INVENTION

According to the present invention, a needlestick prevention device for an injection device having a hollow needle comprises a sheath for attachment to the injection device, the sheath being so constructed and arranged that in a first, inoperative position it sealingly encloses the needle, in a second, operative position a first part of the sheath is removed, a second part remains attached to the injection device, and a third part is pivoted about a hinge means to expose the needle, and in a third, cover position the third part is pivoted about the hinge means to cover at least the tip of the needle, and is retained by the second part.

The device of the invention is simple to manufacture, as it only uses the sheath, and no springs or tracks. It is also simple to use, but without the inherent danger of replacing the sheath over the needle, as the pivotal movement effectively moves the sheath sideways over the needle so that a user does not need to put their hands near the needle. In the cover position the third part is retained by the second part, so that it is difficult to remove the third part again. The device is therefore simple to manufacture and use, and is safe in operation.

The second part is adapted for attachment to a hub which carries the needle. It may be substantially cylindrical.

In the inoperative position the first and third parts extend axially from the second part beyond the end of the needle, to form a substantially cylindrical cover for the needle. The first part may extend round approximately one sixth to one half of the circumference of the cover. At its end remote from the second part, the first part has a projection extending axially beyond the third part. The projection is grasped in order to remove the first part.

The third part may be moved angularly from the inoperative position into the operative position, and from the operative position into the cover position by applying a force to the third part. The third part may have a tongue projecting beyond the tip of the needle in the inoperative position. The third part may be moved by applying a force to the tongue.

In the inoperative position the tip of the needle may be covered by the first part or the third part. The first part may have a projection, at its end remote from the second part, extending radially inwardly to cover the tip of the needle. Alternatively the third part may have a closure member extending radially inwardly to cover the tip of the needle.

The second and third parts are connected by the hinge means and a retaining means, which is engaged in the inoperative position and the cover position. The arrangement is such that in the inoperative position the first part prevents disengagement of the retaining means, but once the first part is removed the retaining means disengages on movement of the third part about the hinge means.

The hinge means may extend round one sixth to one quarter of the circumference of the second part. It is preferably a spring or living hinge, so that, on movement of the third part from the inoperative position and following disengagement of the retaining means, the hinge means acts to move the third part automatically into the operative position. This automatic movement means that the user has to touch the third part only once to move it into the operative position. In the operative position the third part is conveniently as near as possible in line with the injection device, so that it has moved angularly through 180°.

On movement of the third part from the operative position the hinge means acts to move the third part towards the cover position once its angular movement exceeds a predetermined amount. This amount may be between 80° and 100°. The hinge means may move the third part directly into the cover position, so that the user has to touch the third part only once to effect this movement. Alternatively, a further manual force may be applied to move the third part into the cover position. In the cover position the third part moves beyond the inoperative position, and the retaining means engages in a position where a permanent locking arrangement is actuated.

In one embodiment the retaining means comprises at least one pair of corresponding stepped portions on the second and third parts. In the inoperative position the stepped portions of a pair are attached by a weakened portion which is adapted to break when the angular movement of the third part from the inoperative position exceeds a predetermined amount. This amount may be between 30° and 45°. The hinge means may extend between one sixth and one quarter of the circumference of the second part, with the weakened portion accounting for the remaining circumference (approximately two thirds), after removal of the first part.

Preferably two pairs of stepped portions are provided on the second and third parts, the pairs being separated by the hinge means, and the stepped portions of each pair being attached by a weakened portion. This ensures that the weakened portions break easily, and that the hinge means operates correctly.

In the cover position the stepped portion on the third part engages behind the stepped portion on the second part to retain the third part in the cover position. In the cover position the third part has moved beyond the inoperative position, ensuring that it covers the needle, and is retained in that position, so that it is not easy to expose the needle again.

In another embodiment, the retaining means may comprise at least one peg on one of the second or third parts engaging in a complementary slot on the other part. Conveniently the or each peg is provided on the third part, and the or each slot on the second part. The or each peg may have two detents, the first engaging in a recess in a slot in the inoperative position, and the second engaging in the recess in the cover position to provide the permanent locking. There may be two pegs.

In a modification the retaining means may comprise a first mechanism for the inoperative position and a second mechanism for the cover position. For the inoperative position, the first mechanism comprises a projection on one of the second and third parts engaging in a complementary recess on the other part, and for the cover position the second mechanism comprises a peg on one part engaging in a complementary slot on the other part. The projection and the peg may be on different parts. Thus, a projection on the third part may engage in a recess on the second part, and a peg on the second part may engage in a slot on the second part to provide the permanent locking. Conveniently there are two projections and two pegs.

A secondary locking mechanism may also be provided for the needle in the cover position. The secondary mechanism may comprise locking means on the third part allowing the needle to pass through as the third part goes beyond the inoperative position into the cover position, but preventing the needle passing back again. The secondary locking mechanism may comprise a pair of opposing hooks, arranged such that the needle is able to pass between them in one direction, but not in the other.

In order to ensure that it is difficult to remove the whole sheath from the injection device, the sheath is attached to the hub carrying the needle by a locking mechanism. The locking mechanism comprises projections on the sheath or the hub engaging in complementary recesses in the hub or the sheath. Alternatively, the sheath and hub may be made as a single component, for example by injection moulding of plastics material.

The sheath may be moulded as a single component, with the first part sealing against the second and third parts, but not actually fused to them. This is achieved by moulding a small gap around the first part. As the sheath cools it shrinks, but the second and third parts shrink more than the first part, so that the gap disappears, and the first part is retained by the second and third parts. This means that the first part, being sealingly retained but not fused, can be readily removed, like a tear-off strip, when the injection device is to be used. Alternatively, the second and third parts may be moulded as a single component, with the first part being a strip, for example of foil, attached subsequently.

BRIEF DESCRIPTION OF THE DRAWINGS

Various embodiments of the invention are illustrated, by way of example only, in the accompanying drawings, in which:

FIG. 8 is a perspective view of a second needlestick prevention device attached to a hub carrying a needle of an injection device, in an inoperative position;

FIG. 9 is similar to FIG. 8, but shows the device in an operative position;

FIG. 10 is an enlarged perspective view of a portion of FIG. 9;

FIG. 11 is an enlarged perspective view of a further portion of FIG. 9;

FIG. 12 is similar to FIG. 8, but shows the device in a cover position.

FIG. 13 is a perspective view of a third needlestick prevention device in an inoperative position;

FIG. 14 shows the device of FIG. 13 with a first part removed;

FIG. 15 is an enlarged perspective view of a portion of FIG. 14;

DETAILED DESCRIPTION

The needlestick prevention device shown in FIGS. 1 to 7 comprises a sheath 1 for attachment to an injection device, such as a syringe (not shown) with a hollow needle for injecting or removing fluid from a human or animal body. The sheath 1 is shown attached to a hub 2 carrying the needle 3 (see FIGS. 2 and 6). The hub 2 in turn is attached to a syringe in any known way.

The sheath 1 is designed to prevent a user accidentally sticking the needle into him or herself, or indeed another person, either before or after correct use of the syringe. The sheath 1 is injection moulded of plastics material such as polypropylene as a single component, formed from three parts 4,5,6.

Figure 1:
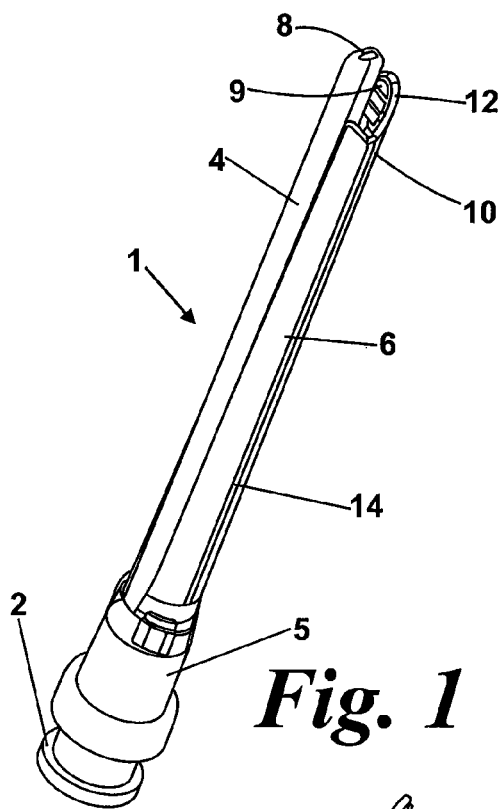
FIG. 1 is a perspective view of a first needlestick prevention device attached to a hub carrying a needle of an injection device in an inoperative position.
Figure 6:
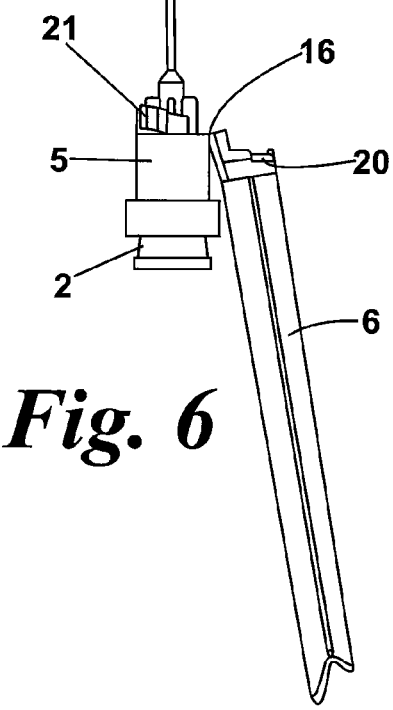
FIG. 6 is a side view of the device in an operative position.
Figure 7:
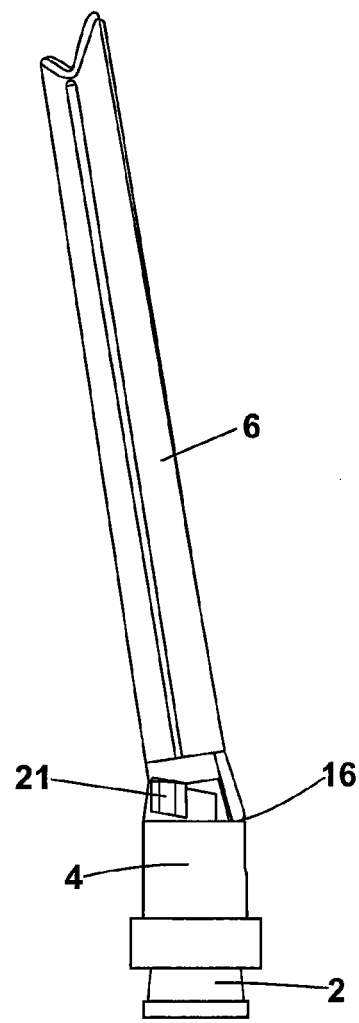
FIG. 7 is a side view of the device in a cover position.

The three parts 4,5,6 can take up three positions. The first, inoperative, position is shown in FIG. 1, where the three parts sealingly enclose the needle 3. The second, operative, position is shown in FIG. 6, where the first part 4 is removed (see FIG. 2), the second part 5 remains attached to the hub 2, and the third part 6 is pivoted to expose the needle 3. The third, cover, position is shown in FIG. 7, where the third part 6 is pivoted back again to cover the needle 3, and is retained by the second part 5.

The second part 5 is substantially cylindrical for attachment to the hub 2 by projections (not shown) on the second part 5 received in recesses (not shown) on the hub 2. While this is a standard way of attaching a sheath to a hub, in this case the projections and recesses are larger and deeper than in a standard attachment, to ensure that it is difficult to pull the sheath 1 off the hub 2. This means that the sheath 1 will be used correctly, and not as a standard sheath, which is normally pulled off the hub to expose the needle for use.

The first part 4 and third part 6 extend axially from the distal end of the second part 5 to form a substantially cylindrical cover for the needle 3. Both the first part 4 and third part 6 extend beyond the needle tip. The first part 4 extends round approximately one sixth of the circumference of the second and third parts 5, 6 in the manner of a tear-off strip. This is achieved in the moulding of the sheath 1, by providing a small gap round the first part 4, which disappears as the sheath 1 cools and shrinks. The first part 4 extends axially beyond the third part 6 at its distal end 8, which carries a radially-inwardly directed projection 9 to seal off the distal end of the sheath 1. The first part 4 is tapered inwardly slightly adjacent the second part 5.

The third part 6 extends round the remaining circumference of the second part 5 (about five-sixths of the circumference). The distal end 10 of the third part 6 is formed with a transverse notch 11, and an internally ribbed tongue 12 on the side of the notch 11 opposite the first part 4. The ribbed tongue 12 is slightly longer than the portions 13 adjacent the first part 4. The projection 9 seals with the third part at the base of the tongue 12. A reinforcing rib 14 extends from the base of the notch 11 on opposing sides of the third part 6 to a point adjacent the second part 5.

Figure 2:
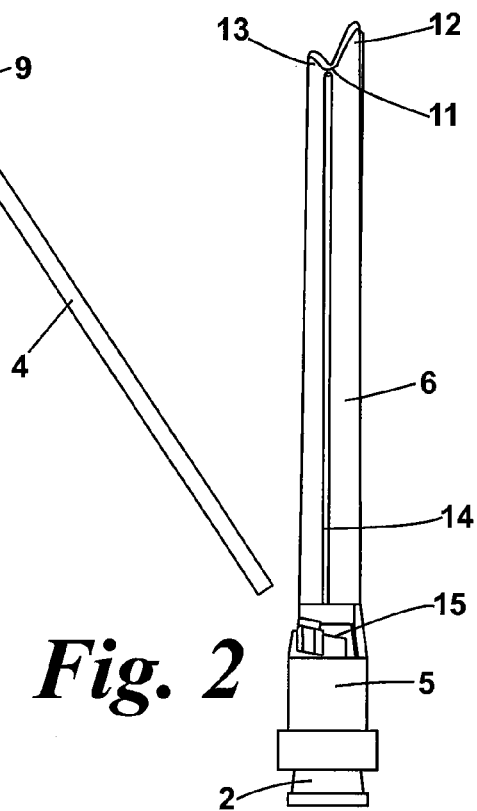
FIG. 2 is a side view of the needlestick prevention device of FIG. 1 with a first part removed.
Figure 3:
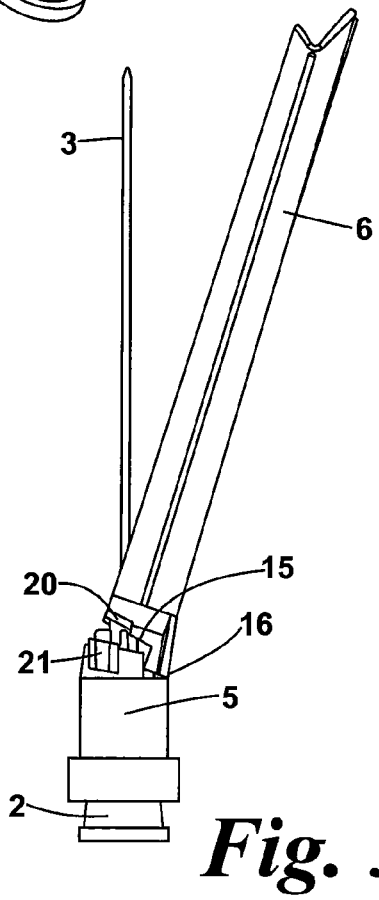
FIG. 3 is a side view similar to FIG. 2, but showing an intermediate position.
Figure 4:
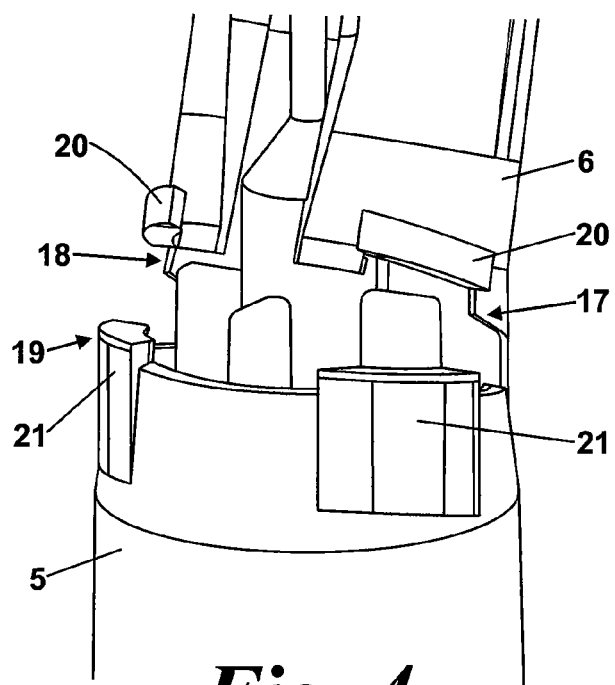
FIG. 4 is an enlarged perspective view of a portion of FIG. 3.
Figure 5:
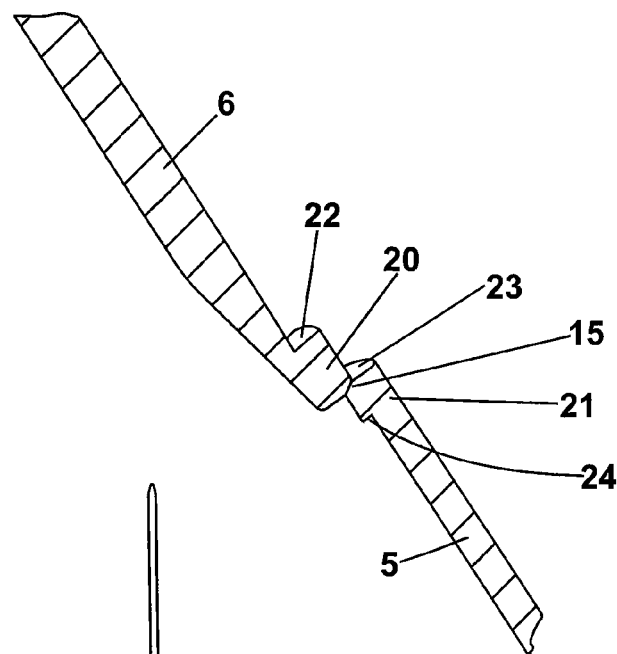
FIG. 5 is a section through part of the wall of the device.

The third part 6 is attached to the second part 5 by a retaining means 19 and a hinge means 16. As best seen in FIGS. 2 to 4, the hinge 16 is opposite the first part 4, and extends between one-quarter and one-sixth of the circumference of the second part 5. The retaining means 19 is in two parts 17,18 separated by the hinge 16. As best seen in FIGS. 4 and 5, each retaining part 17, 18 comprises a radial stepped projection 20 on the third part 6, and a corresponding radial stepped projection 21 on the second part 5, each pair of corresponding radial projections 20,21 being connected by a weakened portion 15. Each radial projection 20 forms an external shoulder 22 on the third part 6. Each radial projection 21 is substantially wedge-shaped, forming an external abutment 23 and an internal shoulder 24 on the second part 5 (see FIG. 5). The radial projections 20, 21 also add to the strength of the construction at the weakened portions 15. Each weakened portion 15 extends from the projections 20, 21 towards the hinge 16, and has a split line generally inclined to the axis of the sheath 1, and stepped axially towards the hinge 16.

When the sheath 1 is moved from the inoperative position into the operative position, as shown in FIGS. 2,3 and 5, movement of the third part 6 towards the injection device firstly causes the weakened portions 15 to break along the split lines. The third part 6 is then connected to the second part 5 only by the hinge 16. This is constructed as a living hinge, so that once the weakened portions 15 have broken, and the third part 6 has moved through an angle of about 90°, the hinge 16 automatically moves the third part 6 into the operative position shown in FIG. 6.

Similarly, when the sheath 1 is to be moved from the operative position of FIG. 6 to the cover position of FIG. 7, the user performs the first part of the movement, but once the third part 6 has moved through an angle of about 90° the hinge 16 will move the third part 6 into the cover position of FIG. 7. It will be noted that in the cover position the third part 6 is over centre, so that it is in contact with the tip of the needle 3, to protect against needlestick. The third part 6 is retained in the cover position by the retaining means 19, with each external shoulder 22 on the third part 6 engaging with the corresponding internal shoulder 24 on the second part 5. It will be appreciated that, in order to achieve this, the second part 5 and third part 6 are deflected relatively in a radial direction. Normally it will be the third part 6 that is deflected radially inwardly, a movement accommodated by the hinge 16. In the cover position the injection device is ready for disposal.

The sheath 1, as mentioned above, is injection moulded with two parts in a single moulding operation, resulting in a single component. The second and third parts 5,6 are moulded as one part, and the first part 4 as a separate part, with a small gap around it. The material shrinks as it cools after moulding, so that the gap disappears and the first part 4 engages sealingly with the second and third parts 5,6, but without being fused to them. Once cooled, the sheath 1 can be mounted on a hub 2 carrying a needle 3, so that the needle 3 is sealingly enclosed.

For use, the hub 2 with the sheath 1 enclosing the needle 3 is attached to an injection device such as a syringe. The sheath 1 is in the inoperative position of FIG. 1. The user then grasps the projection 9 at the distal end of the first part 4, and pulls the first part to remove it from the second and third parts 5,6 (see FIG. 2). There is no danger of the user touching the needle 3, as the projection 9 is located beyond the end of the needle 3. The user discards the first part 4, and then either grasps the tongue 12 or places it on the edge of a convenient solid surface, and applies a force urging the third part 6 away from the needle 3. As the third part moves the weakened portions 15 break, as shown in FIG. 3, leaving the third part 6 attached to the second part 5 by the hinge 16. When the third part has moved through an angle of about 90° the hinge 16 then urges it into the operative position of FIG. 6. The user then gives the injection, and when it is completed applies a force to the free end 10 of the third part 6 to urge it towards the needle 3 again. When the third part has moved through about 90° the hinge 16 urges it into the cover position of FIG. 7, with the shoulders 22 on the third part 6 engaging with the internal shoulders 24 on the second part 5. In this position the third part 6 engages the needle tip and extends beyond it, protecting against the possibility of needlestick. It will be appreciated that there is no danger of a needlestick injury in applying the force to urge the third part 6 into the cover position, as the third part 6 in the operative position is not near the needle tip. It will also be appreciated that the retaining means 19 ensure that the third part 6 cannot readily be moved away from the cover position to expose the needle 3 again.

A second embodiment is shown in FIGS. 8 to 12. This embodiment is a modification of the device of FIGS. 1 to 7, and corresponding reference numerals have been applied to corresponding parts.

Thus, as shown in FIGS. 8 to 12, the sheath 1 is again formed from three parts 4, 5, 6 attached to a hub 2 carrying a needle 3.

The second part 5 is substantially cylindrical and is attached to the hub 2, in this case by being integrally moulded. This means that the sheath 1 will be used correctly, and not as a standard sheath, which is normally pulled off the hub to expose the needle for use.

The first part 4 and third part 6 extend axially from the distal end of the second part 5 to form a substantially cylindrical cover for the needle 3. Both the first part 4 and third part 6 extend beyond the needle tip. The first part 4 extends round approximately one quarter of the circumference of the second and third parts 5, 6 and is provided as a foil tear-off strip. The first part 4 extends axially beyond the third part 6 at its distal end 8, forming a projection 9 which is grasped by the user to remove the first part 4. At its proximal end the first part 4 extends over the second part 5. Both the second part 5 and the third part 6 have flat surfaces (see FIGS. 9 to 11) for attachment of the first part 4.

The third part 6 extends round the remaining circumference of the second part 5 (about three-quarters of the circumference). The distal end 10 of the third part 6 is formed with a closure member 29 to cover the tip of the needle 3.

The hub 2 with the needle 3, and the second and third parts 5, 6 are injection moulded of plastics material as a single component. The foil tear-off strip (first part 4) is attached after moulding, in any suitable way.

The third part 6 is attached to the second part 5 by a retaining means 19 and a hinge means 16, which is a living hinge. As best seen in FIGS. 9 and 10, the hinge 16 is opposite the first part 4, and extends between one-quarter and one-sixth of the circumference of the second part 5. The retaining means 19 is opposite the hinge 16, and in the inoperative position is covered by the first part 4.

The retaining means 19 is best seen in FIGS. 9 and 10, and comprises a peg and slot arrangement. Two pegs 30 are provided on the proximal end of the third part 6, extending axially towards the second part 5, each for engagement in a complementary slot 31 formed in the second part 5. Each peg 30 is arranged adjacent a flat surface 32 of the third part 6, which is formed with a reinforcing rib 33 at the base of each peg 30. An axial slot 34 is formed in the third part 5 adjacent each peg 30, to provide the necessary amount of radial resilience for each peg.

Each peg 30 has two detents 35, 36 projecting outwardly (away from each other), and adapted to engage in a recess (not shown) in the respective slot 31. A first detent 35 is a retaining detent at the free end of the peg 30. The retaining detent 35 has a rounded profile 37, so that it can disengage from the recess. In the inoperative position the first detent 35 is engaged in the recess, from where it can be disengaged on movement of the third part 6 to the operative position. The second detent 36 is adjacent the base of the peg 30, and has a fir tree profile 38, with an inclined face 39 and a flat face 40, perpendicular to the axis of the third part. The second detent 36 is a locking detent, which will not disengage from the recess. The second detent 36 engages in the recess when the third part 6 moves into the cover position, to provide permanent locking.

The third part 6 also has a pair of inclined ledges 41 (only one of which is shown). Each ledge 41 extends from the hinge 16 towards one of the pegs 30. The ledges 41 form a stop for the third part 6 when it moves into the cover position, in order to define that position and to ensure that the locking detents 36 on the pegs 30 engage in the recesses.

FIG. 11 shows a secondary locking mechanism 42 for the needle 3. The secondary locking mechanism comprises a pair of hooks 43 provided on the internal surface of the third part 6. A gap 44 is defined between the free ends of the hooks 43, the arrangement being such that the needle 3 can deflect the hooks 43 resiliently to allow it to pass through the gap 44. The hooks 43 then return to their original positions, in which the needle 3 cannot pass back through the gap 44. This locks the needle 3 into the third part in the cover position.

The cover position is shown in FIG. 12, with the third part 6 over centre, the pegs 30 locked in the slots 31, and a proximal part 45 of the third part 6 between the ledge 41 and the free edge deformed outwardly.

For use, the hub 2 with the sheath 1 enclosing the needle 3 is attached to an injection device such as a syringe. The sheath 1 is in the inoperative position of FIG. 8 with the retaining detents 35 engaged in the recesses. While the first part 4 is in position, the third part 6 cannot move, as the first part 4 ensures it is connected to the second part 5. The user then grasps the projection 9 at the distal end of the first part 4, and pulls the first part to remove it from the second and third parts 5, 6. There is no danger of the user touching the needle 3 as the projection 9 is located beyond the end of the needle 3. The removal of the first part 4 enables the third part 6 to move relative to the second part 5. The user discards the first part 4, and then grasps the third part 6 and applies a force urging the third part 6 away from the needle 3. As the third part 6 moves the retaining detents 35 disengage from the recesses, leaving the third part 6 attached to the second part 5 by the hinge 16. When the third part has moved through an angle of about 90° the hinge 16 then urges it into the operative position of FIG. 9. The user then gives the injection, and when it is completed applies a force to the free end of the third part 6 to urge it towards the needle 3 again. There is no danger of a needlestick injury in applying the force to urge the third part 6 into the cover position, as the third part 6 in the operative position is not near the needle tip. When the third part has moved through about 90° the hinge 16 urges it back towards the inoperative position. The user applies a further force to move the third part 6 into the cover position of FIG. 12. There is no danger of the user touching the point of the needle 3, as in the inoperative position the point is protected by the closure member 29. The ledges 41 engage with the second part 5 to define the cover position. This is about 8° over centre, and is sufficient to force the locking detents 36 on the pegs 30 on the third part 6 into engagement in the recesses on the second part 5. The needle 3 also passes through the gap 44 of the secondary locking mechanism. In the cover position the third part 6 engages the needle tip and extends beyond it, protecting against the possibility of needlestick. It will be appreciated that the locking detents 36 ensure that the third part 6 cannot readily be moved away from the cover position to expose the needle 3 again.

A third embodiment is shown in FIGS. 13 to 19. This is a modification of the device shown in FIGS. 8 to 12, and corresponding reference numerals have been applied to corresponding parts.

As with the embodiment of FIGS. 8 to 12, the sheath 1 is formed of three parts 4, 5, 6, of which the second and third parts 5, 6 are moulded integrally with the hub 2 carrying the needle 3. The first part 4 is a foil tear-off strip. The hub 2 is shown attached to an injection device 100.

In this embodiment the second part 5 has a rectangular external profile, and the third part 6 has a correspondingly-shaped base 50 for engagement with the second part 5. Internally the second part 5 accommodates the hub 2 for the needle 3. The third part 6 has a substantially U-shaped portion 51 extending axially from three sides of the base 50 to form the cover for the needle 3, completed by the first part 4. The first and third parts 4, 6 each extend beyond the needle tip, with the third part 6 having a chamfered distal end 52. The first part 4 extends axially beyond the third part 6 at its distal end, forming a projection 9 which is grasped by the user to remove the first part 4. At its proximal end the first part 4 extends over the fourth, open side 53 of the base 50 and the corresponding open side 54 of the second part 5. The second part 5 and third part 6 each have flat surfaces, co-planar in the inoperative position, for attachment of the first part 4. The first part 4 is attached to the second and third parts in any suitable way.

Figure 16:
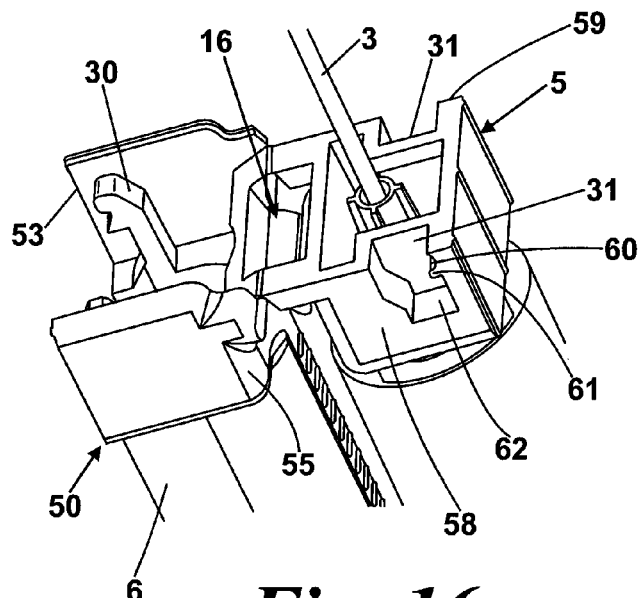
FIG. 16 is similar to FIG. 15, but in an operative position.

The third part 6 is attached to the second part 5 by the retaining means 19, and the hinge means 16, which as before is a living hinge. As best seen in FIG. 16, the hinge 16 is provided on the side 55 of the base 50 opposite the open side 53. The other two sides 56, 57 of the base 50 extend over the corresponding sides 58, 59 of the second part 5, and their internal surfaces engage sealingly with the external surfaces of the second part 6.

The retaining means 19 is best seen in FIG. 15 and 16, and comprises a modified peg and slot arrangement. Two pegs 30 again extend from the third part 6 towards the second part 5, but are accommodated within the base 50. As with the previous embodiment each peg has two detents 35, 36, but these project towards the open side 53, rather than away from each other. The shape and function of the detents 35, 36 is otherwise the same as that of the previous embodiment.

Figure 17:
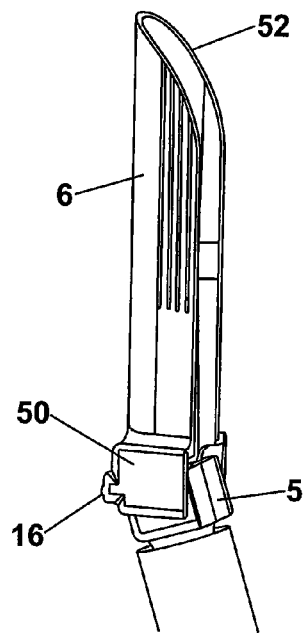
FIG. 17 shows the device of FIG. 13 in a cover position.
Figure 18:
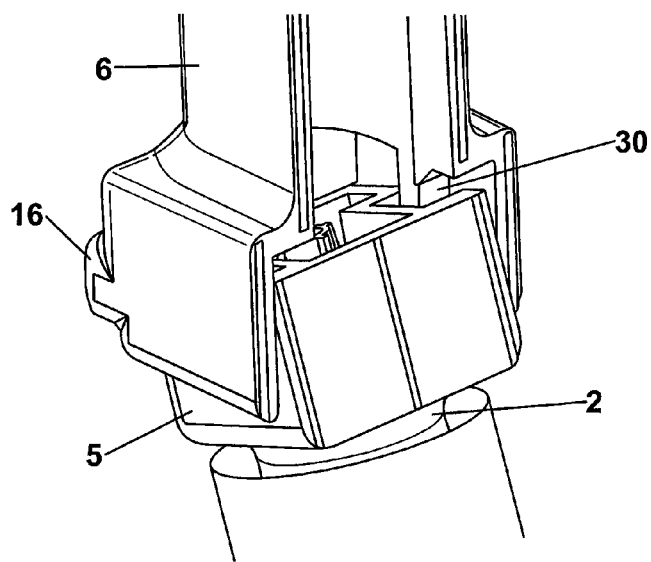
FIG. 18 is an enlarged view of a portion of FIG. 17.

Each peg 30 has a complementary slot 31 formed externally on a respective side 58, 59 of the second part 5. In each slot 31 a recess 60 is defined at the open distal end by a projection 61. The proximal base end 62 of each slot 31 is closed, and extends below the projection 61 to accommodate the peg 30 in the cover position. The base 62 of each slot 31 forms a stop for the third part 6 when it moves into the cover position, in order to define that position, in which the locking detent 36 engages below the projection 61. This position is shown in FIGS. 17 and 18. FIG. 14 shows the retaining means 19 in the inoperative position, in which the retaining detents 35 on the pegs 30 engage sealingly in the open ends of the slots 31. FIG. 15 shows the retaining means 19 with the pegs 30 just out of the slots 31, while FIG. 16 shows the device in the operative position.

Figure 19:
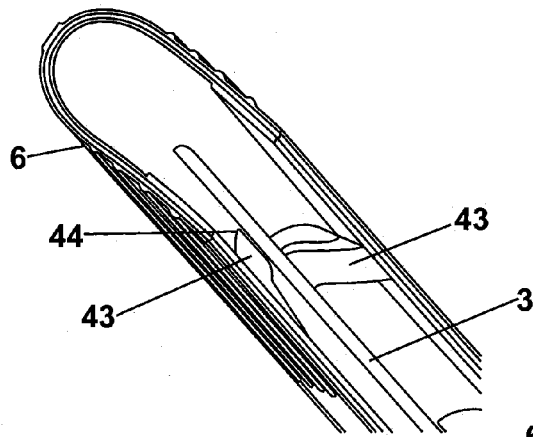
FIG. 19 shows a further portion of FIG. 14.

FIG. 19 shows the secondary locking mechanism 42, as the hooks 43 provided on the third part 6, in a similar manner to FIG. 11.

In use, the embodiment of FIGS. 13 to 19 operates in a very similar way to that of FIGS. 8 to 12. The only difference lies in the movement into the cover position. As before, a force applied to the third part in the operative position (FIG. 16) urges the third part 6 towards the needle 3 again, and when the third part 6 has moved through about 90° the hinge 16 urges it towards the inoperative position (FIG. 15). The user then applies a further force to move the third part 6 into the cover position of FIGS. 17 and 18, where the point of the needle 3 is protected by the end 52 of the third part 6. The pegs 30 enter the slots 31, and the movement continues until the free ends of the pegs 30 engage the bases 62 of the slots, in which position the locking detents 36 engage below the projections 61, to lock the third part 6 against movement away from the cover position in a direction to expose the needle 3 again. The needle 3 is also locked by the secondary locking mechanism 42.

Figure 20:
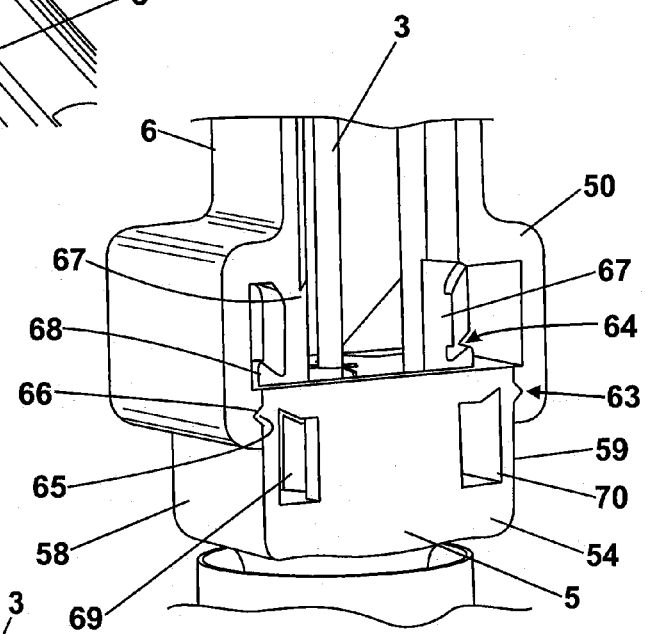
FIG. 20 is a perspective view of a portion of a modified needlestick prevention device in an inoperative position.
Figure 21:
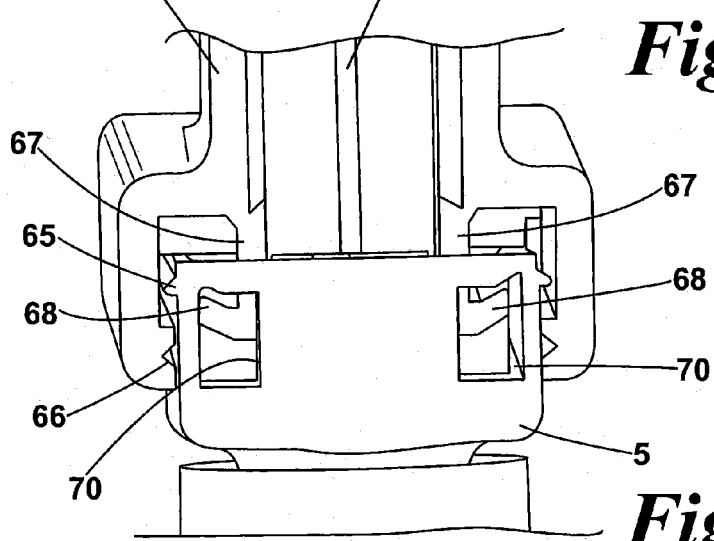
FIG. 21 is similar to FIG. 20, but with the device in a cover position.

FIGS. 20 and 21 show a modification of the embodiment of FIGS. 13 to 19. The modification is to the retaining means 19. In this embodiment the retaining means 19 has a first mechanism 63 for the inoperative position, and a second mechanism 64 for the cover position. The first mechanism 63 comprises an externally projecting rib 65 of triangular profile formed on each of the sides 58, 59 of the second part 5, and adapted to engage in a complementary recess 66 in the internal surface of each of the sides 56, 57 of the base 50. Each rib 63 extends only part of the way along the side 58 or 59. The engagement of the ribs 65 in the recesses 66 will maintain the second and third parts 5, 6 in position until the manual force is applied to the third part 6 move it into the operative position.

The second mechanism 64 provides locking in the cover position, and comprises a peg and slot arrangement. Two pegs 67 are provided on the third part 6, extending axially towards the second part 5, and essentially parallel to the needle 3. Each peg 67 terminates in an outward-facing hook 68. Each peg 67 is adapted to slide in an axial slot 69 formed internally in the second part 5, adjacent the open side 54. Each slot 69 has an aperture 70 whose shape is complementary to the hook 68 on the respective peg 67. The second part 5 also has stop ribs (not shown) extending internally on each side 58, 59 from the open side 54 towards the hinge 16. On movement of the third part 6 into the cover position each peg 67 moves axially into the second part 5. Each hook 68 engages with a respective stop rib, which urges it resiliently towards the other hook 68 so that it is inclined to the needle 3. On further axial movement each hook 68 moves past the stop rib and is returned by its resilience to its position parallel to the needle 3, and enters the respective aperture 70. The hooks 68 are then locked in the apertures 70, since the stop ribs are constructed to prevent movement of the hooks 68 in the reverse direction. The stop ribs thus provide a stop for the third part 6 when it moves into the cover position, in order to define that position and to ensure that the second mechanism 64 operates to provide the locking.

For use, the hub 2 with the sheath 1 enclosing the needle 3 is attached to an injection device such as a syringe 100. The sheath 1 is in the inoperative position of FIG. 20 with the retaining ribs 65 engaged in the recesses 66. While the first part 4 is in position, the third part 6 cannot move, as the first part 4 ensures it is connected to the second part 5. The user then grasps the projection 9 at the distal end of the first part 4, and pulls the first part to remove it from the second and third parts 5, 6. There is no danger of the user touching the needle 3 as the projection 9 is located beyond the end of the needle 3. The removal of the first part 4 enables the third part 6 to move relative to the second part 5. The user discards the first part 4, and then grasps the third part 6 and applies a force urging the third part 6 away from the needle 3. As the third part 6 moves the ribs 65 disengage from the recesses 66, leaving the third part 6 attached to the second part 5 by the hinge 16. When the third part has moved through an angle of about 90° the hinge 16 then urges it into the operative position. The user then gives the injection, and when it is completed applies a force to the free end of the third part 6 to urge it towards the needle 3 again. There is no danger of a needlestick injury in applying the force to urge the third part 6 into the cover position, as the third part 6 in the operative position is not near the needle tip. When the third part has moved through about 90° the hinge 16 urges it back towards the inoperative position. The user applies a further force to move the third part 6 into the cover position of FIG. 21. There is no danger of the user touching the point of the needle 3, as in the inoperative position the point is protected by the end 52 of the third part 6. The ribs 65 move into and then out of the recesses 66, and then the hooks 68 move over the stop ribs, being deflected resiliently by them, and then engage in the locking apertures 70, to define the cover position. This is about 8° over centre. The needle 3 also passes through the gap 44 of the secondary locking mechanism. In the cover position the third part 6 engages the needle tip and extends beyond it, protecting against the possibility of needlestick. It will be appreciated that the locking mechanism 64 ensures that the third part 6 cannot readily be moved away from the cover position to expose the needle 3 again.

In all the embodiments the sheath 1 thus provides a needlestick prevention device which is simple to manufacture and to use.

The invention claimed is:

1. A needlestick prevention device for an injection device having a hollow needle comprises a sheath for attachment to said injection device, said sheath having first, second and third parts, and being so constructed and arranged that in a first, inoperative position said sheath sealingly encloses said needle, in a second, operative position said first part of the sheath is removed, said second part remains attached to said injection device, and said third part is pivoted about a hinge to expose said needle, and in a third, cover position said third part is pivoted about said hinge to cover at least the tip of said needle, and is retained by said second part, said second and third parts are connected by said hinge and a retaining portion, said retaining portion being engaged in said inoperative position and said cover position, said retaining portion comprises at least one pair of stepped portions on said second and third parts, wherein in said inoperative position said stepped portions are attached to each other by a weakened portion, said weakened portion being adapted to break when the angular movement of said third part from said inoperative position exceeds a predetermined amount.

2. A needlestick prevention device as claimed in claim 1, wherein said second part is adapted for attachment to a hub which carries said needle.

3. A needlestick prevention device as claimed in claim 1, wherein in said inoperative position said first and third parts extend axially from said second part beyond the end of said needle, to form a substantially cylindrical cover for said needle.

4. A needlestick prevention device as claimed in claim 1, wherein at its end remote from said second part, said first part has a projection extending axially beyond said third part.

5. A needlestick prevention device as claimed in claim 1, wherein said third part is movable angularly from said inoperative position into said operative position, and from said operative position into said cover position by applying a force to said third part.

6. A needlestick prevention device as claimed in claim 1, wherein said hinge is constructed such that, on movement of said third part from said inoperative position and following disengagement of said retaining portion, said hinge acts to move said third part automatically into said operative position.

7. A needlestick prevention device as claimed in claim 1, wherein on movement of said third part from said operative position said hinge acts to move said third part towards said cover position once its angular movement exceeds a predetermined amount.

8. A needlestick prevention device as claimed in claim 1, wherein in said cover position said third part is beyond said inoperative position, and said retaining portion engages in a position where a permanent locking arrangement is actuated.

9. A needlestick prevention device as claimed in claim 1, wherein two pairs of stepped portions are provided, said pairs being separated by said hinge and said stepped portions of each said pair being attached by the weakened portion.

10. A needlestick prevention device as claimed in claim 1, wherein in said cover position the or each said stepped portion on said third part engages behind the respective said stepped portion on said second part to retain said third part in said cover position.

11. A needlestick prevention device as claimed in claim 1, wherein a secondary locking mechanism is provided for said needle in said cover position.

* * * * *